(12) United States Patent
Lin

(10) Patent No.: US 11,100,779 B1
(45) Date of Patent: Aug. 24, 2021

(54) COMPREHENSIVE CARE DEVICE

(71) Applicant: New Century Products Limited, Taipei (TW)

(72) Inventor: Fu-Tsun Lin, Taipei (TW)

(73) Assignee: NEW CENTURY PRODUCTS LIMITED, Taipei (TW)

( * ) Notice: Subject to any disclaimer, the term of this patent is extended or adjusted under 35 U.S.C. 154(b) by 0 days.

(21) Appl. No.: 17/088,587

(22) Filed: Nov. 4, 2020

(51) Int. Cl.
*G16H 40/67* (2018.01)
*G08B 21/22* (2006.01)
*G08B 21/02* (2006.01)

(52) U.S. Cl.
CPC ...... *G08B 21/0211* (2013.01); *G08B 21/0288* (2013.01); *G16H 40/67* (2018.01)

(58) Field of Classification Search
CPC .................................................. G08B 21/0211
See application file for complete search history.

(56) References Cited

U.S. PATENT DOCUMENTS

| | | | | |
|---|---|---|---|---|
| 2009/0264714 | A1* | 10/2009 | Chou | A61B 5/0002 600/301 |
| 2015/0018660 | A1* | 1/2015 | Thomson | A61B 5/332 600/393 |
| 2017/0258358 | A1* | 9/2017 | Bishay | A61B 5/7475 |
| 2019/0125296 | A1* | 5/2019 | Keidar | A61B 5/0205 |
| 2019/0328320 | A1* | 10/2019 | Lim | A61B 5/4806 |
| 2020/0206511 | A1* | 7/2020 | Goedeke | A61B 5/021 |
| 2020/0337651 | A1* | 10/2020 | Kwan | A61B 5/00 |
| 2020/0408876 | A1* | 12/2020 | Weber | H02J 50/10 |

* cited by examiner

*Primary Examiner* — Joseph H Feild
*Assistant Examiner* — Pameshanand Mahase
(74) *Attorney, Agent, or Firm* — Leong C. Lei

(57) ABSTRACT

The present invention provides a comprehensive care device comprising a case, a fixing element for fixing the case, sensing elements, a storage element, a processing element, a data transmission element and a power supply element. Each sensing element is used to sense physiological state values of the care object to generate physiological state signals. The storage element stores the physiological state signals sensed by the sensing elements. The processing element receives the physiological state signals stored in the storage element to perform a signal calculation, and then compare with a preset value to determine whether generate a warning signal or not. The data transmission element transmits the physiological state signals to a portable device; and the power supply element provides an electric power with the comprehensive care device. Therefore, the comprehensive care device of the present invention can provide real-time monitoring and care of the care object.

9 Claims, 7 Drawing Sheets

COMPREHENSIVE CARE DEVICE

TECHNICAL FIELD OF THE INVENTION

The present invention relates to a comprehensive care device, and more particularly to a comprehensive care device capable of sensing physiological values for the elderly, adults, children or pets.

DESCRIPTION OF THE PRIOR ART

With the advancement of medical technology, the average life-time of human beings has gradually increased, so that health care has become an important social demand in the future, especially remote health care is an active and effective way of health care. In addition, modern people often face the psychological pressure of job competition and neglect to manage their own health, which makes overwork and chronic diseases younger. Therefore, as the demand for care is increasing but the care resources are quite limited, it is necessary to provide diversified health care methods.

In recent years, the trend towards fewer children has caused parents to pay more attention to the care of infants and young children. Infants and young children lack the ability to take care of themselves, so they need to be taken care of for long. For example, the sleeping position of infants and young children will affect the smooth breathing, and the heads of infants and young children are relatively soft, and they need a good sleeping posture to facilitate the development of the head. In addition, the best sleeping position for infants and young children is to lie on their backs or on their sides to avoid compression of the chest and lungs. Therefore, doctors recommend lying on their sides after feeding to prevent the baby from choking on milk or coughing. When the baby chokes on milk, the breathing may stop or become disordered, but the baby's heartbeat will not stop immediately. Further, the heartbeat will be accelerated, and it is difficult to judge the possibility of life-threatening. Therefore, it may not be enough to judge the physiological condition by the heartbeat.

Due to the needs of infants, young children, or elderly care, real-time sensing, and remote monitoring of the physiological information of infants, young children or the elderly are in urgent need of technology development. At present, most of the commercially available sensing devices use adhesive contact measurement devices, such as adhesive electrode pad. However, this kind of adhesive electrode pad is easy to cause skin allergies, and it is easy to fall off when infants, young children or the elderly turn over and it generates false signals.

In view of this, the inventor has invested a lot of research, development and effort, making breakthroughs and innovations, hoping to solve the current shortcomings with novel technical methods, not only bringing better products to the society, but also promoting industrial development at the same time.

SUMMARY OF THE INVENTION

In view of the aforementioned needs for immediate monitoring and care of infants, young children or the elderly, the main purpose of the present invention is to provide a non-contact comprehensive care device, which is small in size and light in weight to avoid discomfort and can monitor the physiological status of infants, young children or the elderly to give appropriate reminders to caregivers.

To achieve the above objective, the present invention provides a comprehensive care device comprising a case, a fixing element, sensing elements, a storage element, a processing element, a power supply element, and a data transmission element; wherein the case has an accommodating space, and the fixing element is disposed on an external surface of the case to be fixed on the clothing or body of a care object. Secondly, the sensing elements are installed in the accommodating space, and each sensing element is used to sense physiological state values of the care object to generate physiological state signals based on the physiological state values. Further, the storage element is installed in the accommodating space and is electrically connected to the sensing elements for storing the physiological state signals of the care object sensed by the sensing elements. Moreover, the processing element is installed in the accommodating space and is electrically connected to the storage element for receiving the physiological state signals of the care object stored in the storage element to perform a signal calculation, and then compare with a preset value to determine whether generate a warning signal or not. In addition, the power supply element is installed in the accommodating space and is electrically connected to the sensing elements, the storage element, and the processing element, so as to provide an electric power with an operational function of the comprehensive care device. Furthermore, the data transmission element is installed in the accommodating space and is electrically connected to the processing element and the power supply element, and transmits the physiological state signals of the care object to a portable device through a wireless communication method. When the processing element determines that the warning signal needs to be sent out, the data transmission element transmits the warning signal to the portable device, so that the portable device displays the warning signal.

In some embodiments, the portable device has a user interface for inputting an observation value of the care object by a user, and the observation value is transmitted to the processing element through the data transmission element. Further, the observation value and the physiological state signal are performed the signal calculation to compare with the preset value to determine whether the warning signal is generated.

In some embodiments, the sensing elements include at least one element selected from the group consisting of a radar sensing element, a temperature sensing element, an inertial measurement unit, a global positioning system sensing element, and a pressure sensing element.

In some embodiments, the radar sensing element is used to sense a respiration value of the care object, and a respiratory frequency or abdominal fluctuations of the care object are calculated by the processing element to determine the respiration state of the care object. When the processing element determines that the respiratory frequency is abnormal, the processing element generates the warning signal.

In some embodiments, the radar sensing element is used to sense a heartbeat value of the care object, and when the processing element determines that the heartbeat value exceeds a preset value range, the processing element generates the warning signal.

In some embodiments, the inertial measurement unit is composed of three-axis gyroscopes and three-directional accelerometers and is used to detect a tilt angle.

In some embodiments, the radar sensing element measures a plurality of heartbeat values and a plurality of respiratory frequency at different times, and the processing element receives the heartbeat values and the respiratory frequency and calculates them through the signal calculation to identify whether the heartbeat values and the respiratory frequency belong to a waking state or not for a period of time. Further, the processing element analyzes the average and sum of sleep by detecting the time of the heartbeat values in the sleeping state.

In some embodiments, the fixing element is a clamp or a fixing structure; wherein the fixing structure comprises a fixed belt and a fastener, and the cast is fixed on the fixed belt; wherein the fastener is composed of a male fastener and a female fastener, and the male fastener is correspondingly fastened to the female fastener. Alternatively, the fastener is composed of a sticky part and a bonding part corresponding to the sticky part, and the sticky part is correspondingly bonded to the bonding part.

In some embodiments, the wireless communication method is one of bluetooth communication protocol, wireless network communication protocol, wireless RF communication, broadband network communication, Zigbee, Thread, 3G communication protocol or 4G communication protocol.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE PREFERRED EMBODIMENTS

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

Figure 1:
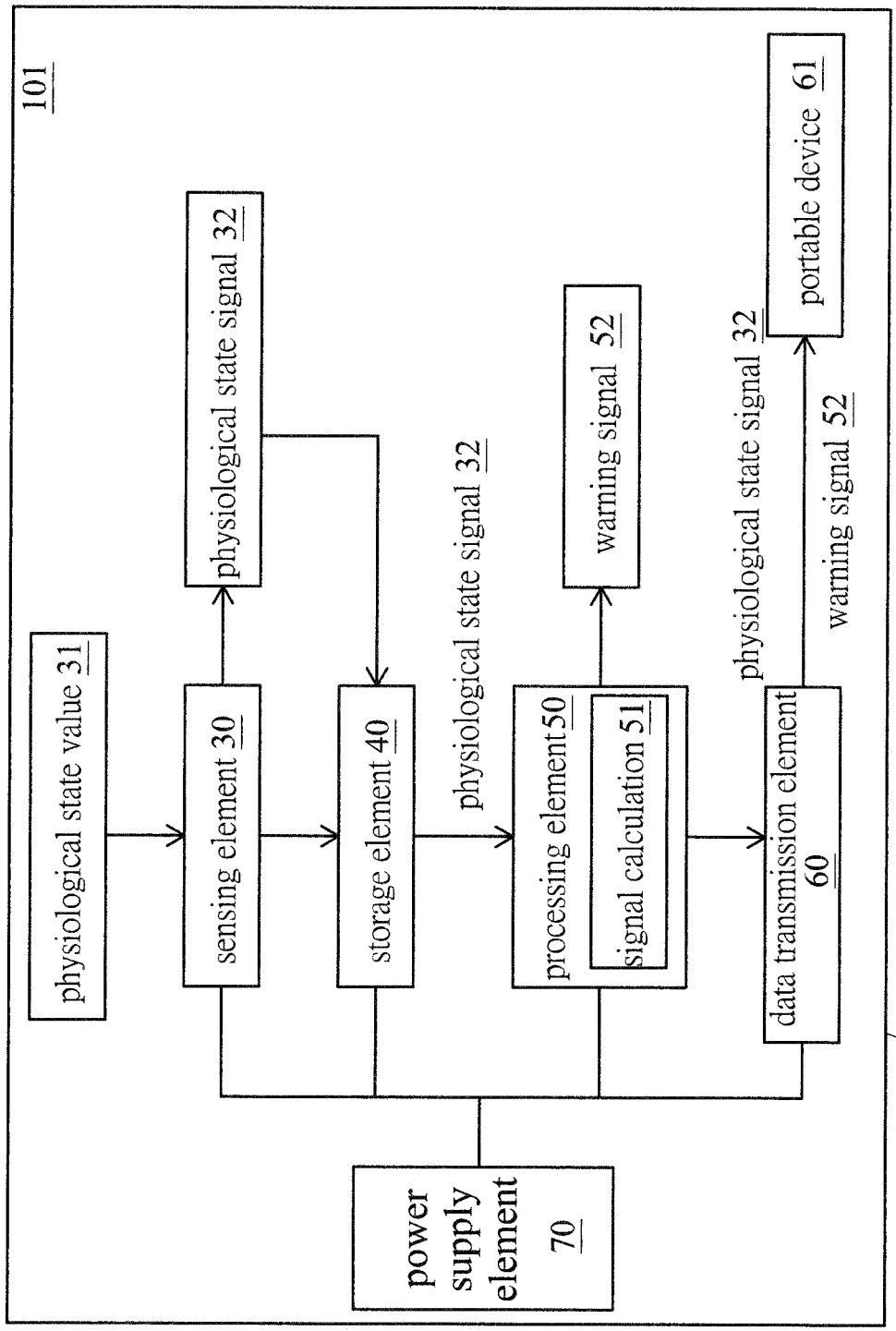
FIG. 1 is a schematic view of a comprehensive care device according to a first embodiment of the present invention.
Figure 2:
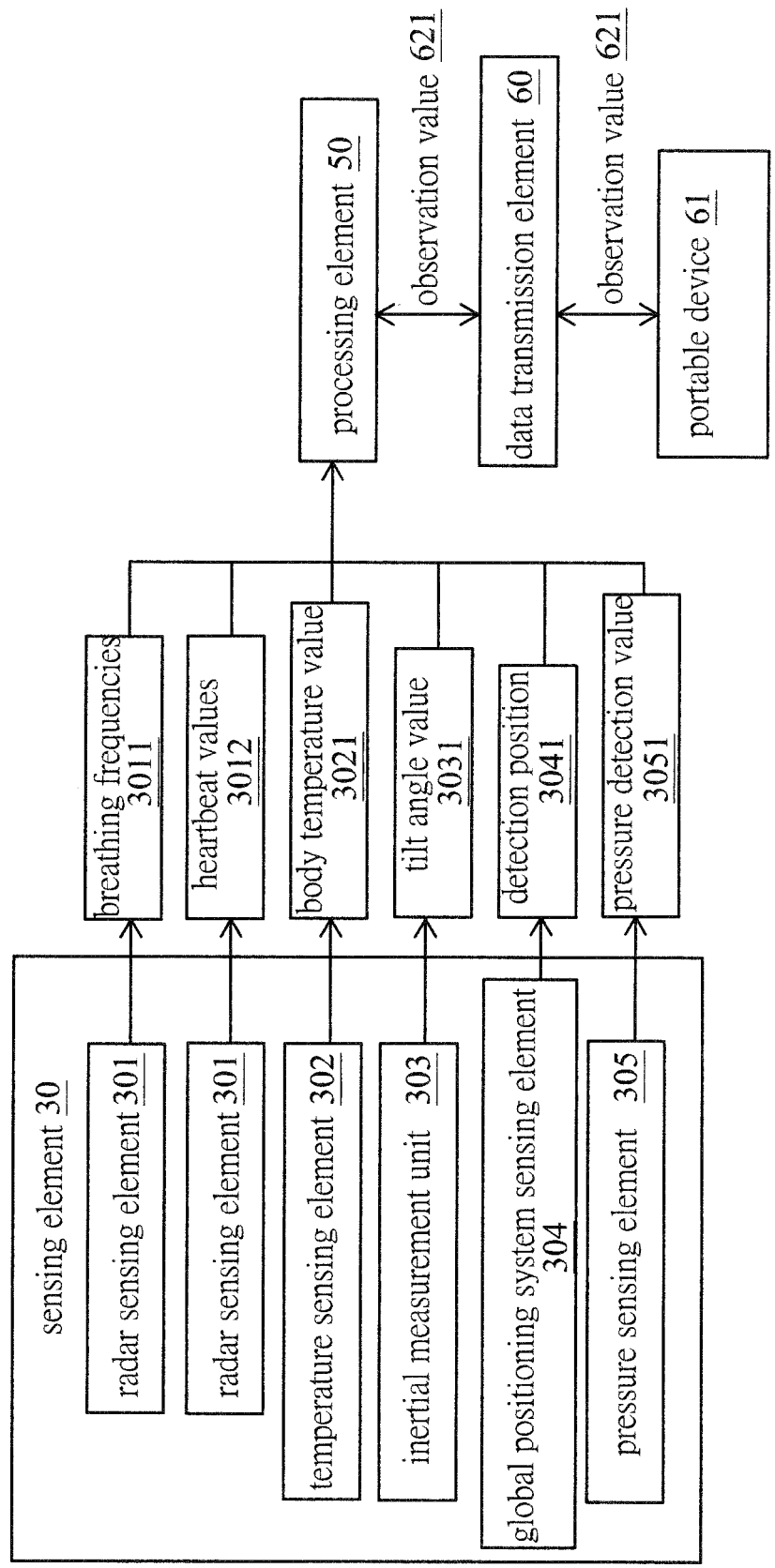
FIG. 2 is a schematic view of the comprehensive care device according to a second embodiment of the present invention.
Figure 3:
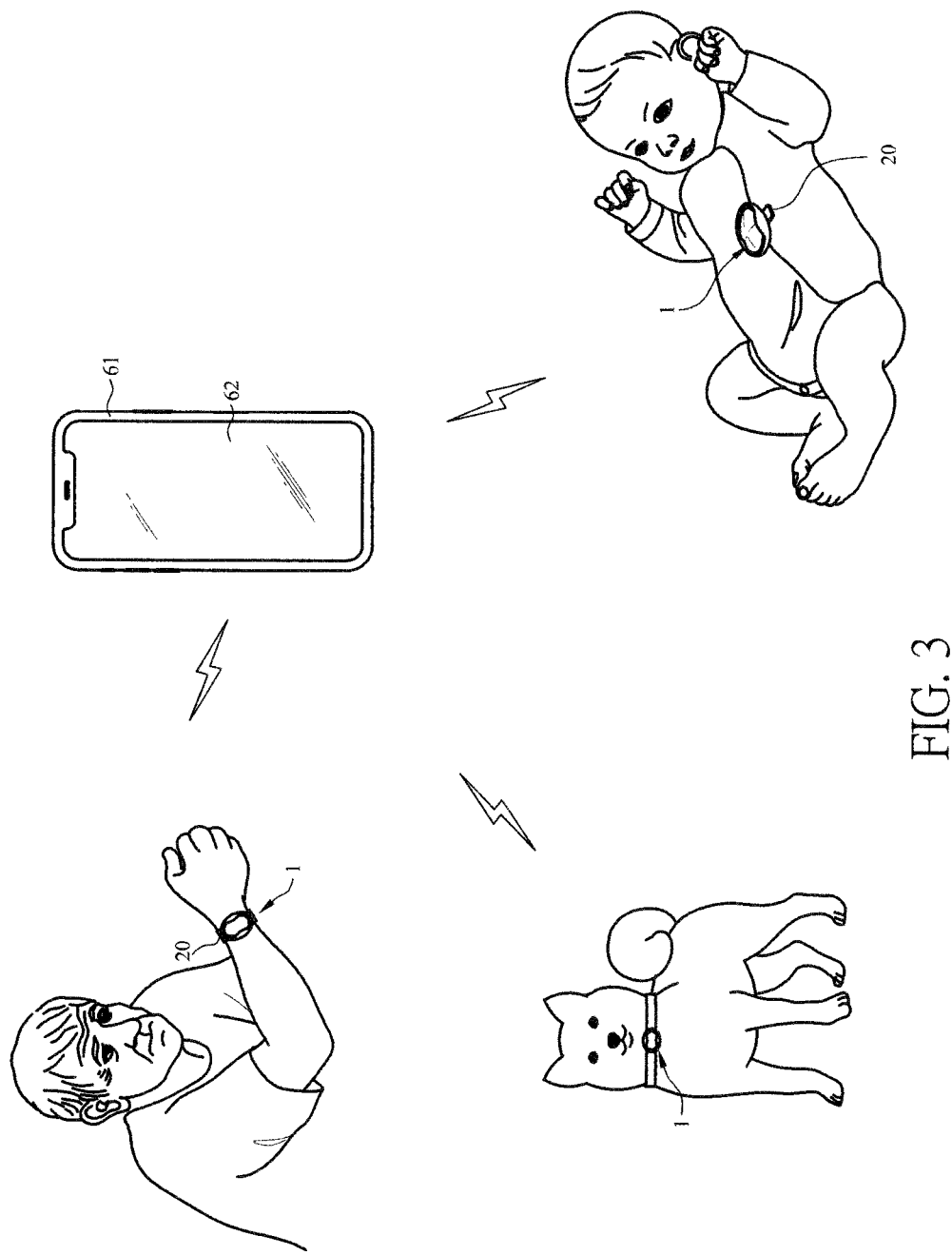
FIG. 3 is a schematic diagram of a wireless communication method between the comprehensive care device and a portable device according to the first embodiment of the present invention.

Please refer to FIG. 1 to FIG. 3, FIG. 1 is a schematic view of a comprehensive care device according to a first embodiment of the present invention; FIG. 2 is a schematic view of the comprehensive care device according to a second embodiment of the present invention, and FIG. 3 is a schematic diagram of a wireless communication method between the comprehensive care device and a portable device according to the first embodiment of the present invention.

As shown in FIG. 1 to FIG. 3, the present invention provides a comprehensive care device 1 comprising a case 10 having an accommodating space 101, a fixing element 20, sensing elements 30, a storage element 40, a processing element 50, a data transmission element 60, and a power supply element 70; wherein the fixing element 20 is disposed on an external surface of the case 10 to be fixed on the clothing or body of a care object, and the care object can be an infant, an adult, an elderly or a pet. Secondly, the sensing elements 30 are installed in the accommodating space 101, and each sensing elements 30 is used to sense physiological state values 31 of the care object to generate physiological state signals 32 based on the physiological state values 31. Further, the storage element 40 is installed in the accommodating space 101 and is electrically connected to the sensing elements 30 for storing the physiological state signals 32 of the care object sensed by the sensing elements 30. Moreover, the processing element 50 is installed in the accommodating space 101 and is electrically connected to the storage element 40 for receiving the physiological state signals 32 of the care object stored in the storage element 40 to perform a signal calculation 51, and then compare with a preset value to determine whether generate a warning signal or not. Furthermore, the data transmission element 60 is installed in the accommodating space 101 and is electrically connected to the processing element 50, and transmits the physiological state signals 32 of the care object to a portable device 61 through a wireless communication method. When the processing element 50 determines that the warning signal 52 needs to be sent out by a buzzer, the data transmission element 60 transmits the warning signal 52 to the portable device 61, so that the portable device 61 displays the warning signal 52; wherein the wireless communication method is one of Bluetooth communication protocol, wireless network communication protocol, wireless RF communication, broadband network communication, Zigbee, Thread, 3G communication protocol or 4G communication protocol. Furthermore, the portable device 61 can be a computer device, a mobile phone device, a tablet computer device or an electronic device that can be monitored in real time, but the present invention is not limited thereto. In addition, the power supply element 70 is installed in the accommodating space 101 and is electrically connected to the sensing elements 30, the storage element 40, the processing element 50 and the data transmission element 60, so as to provide an electric power for an operation function of the comprehensive care device 1.

As shown in FIG. 1 to FIG. 3, the portable device 61 has a user interface 62 for inputting an observation value 621 of the care object by a user, and the observation value 621 is transmitted to the processing element 50 through the data transmission element 60. Further, the observation value 621 and the physiological state signal 32 are performed the signal calculation to compare with the preset value to determine whether the warning signal 52 is generated or not; wherein the observation value 621 includes a height, a weight, a head size, an ambient temperature, number of meals, number of diaper changes, stool frequency, or stool color of the care object.

Furthermore, the sensing elements 30 include at least one element selected from the group consisting of a radar sensing element 301, a temperature sensing element 302, an inertial measurement unit 303, a global positioning system sensing element 304, and a pressure sensing element 305; wherein the radar sensing element 301 is used to sense a respiration value of the care object, and a respiratory frequency or abdominal fluctuations of the care object are calculated by the processing element 50 to determine the respiration state of the care object. When the processing element 50 determines that the respiratory frequency is abnormal, the processing element 50 generates the warning signal 52. In addition, the radar sensing element 301 is used to sense a heartbeat value 3012 of the care object, and when the processing element 50 determines that the heartbeat value 3012 exceeds a preset value range, the processing element 50 generates the warning signal 52. Furthermore, the temperature sensing element 302 is disposed on the surface of the case 10 to obtain a body temperature value 3021 of the care object, and the temperature sensing element 302 is electrically connected to the processing element 50. The processing element 50 determines that the body temperature value 3021 exceeds a preset value, so that the processing element 50 generates the warning signal 52. The inertial measurement unit 303 is composed of three-axis gyroscopes and three-directional accelerometers to form an angle detection element for detecting a tilt angle value 3031. In addition, the inertial measurement unit 303 can assist in detecting the baby's movement posture, such as sleeping on the back, sleeping on the side, and turning over to understand the baby's movement posture. In addition, the global positioning system sensing element 304 continuously or periodically detects the position of the care object, and records the detection time at the same time. The global positioning system sensing element 304 detects a detection position 3041 of the care object and records the time information before sending it to the processing element 50, and the detection position and time are transmitted to the portable device 61 through the data transmission element 60.

The radar sensing element 301 measures a plurality of heartbeat values 3012 and a plurality of respiratory frequency 3011 at different times, and the processing element 50 receives the heartbeat values 3012 and the respiratory frequency 3011 and calculates them through the signal calculation 51 to identify whether the heartbeat values 3012 and the respiratory frequency 3011 belong to a waking state or not for a period of time. Further, the processing element 50 analyzes the average and sum of sleep by detecting the time of the heartbeat values 3012 in the sleeping state. In addition, the baby's state is confirmed by detecting the heartbeat values 3012 and the respiratory frequency 3011, and the average sleep hours and average hours of activity can be analyzed.

In addition, when the care object is a pet, the comprehensive care device 1 can be used as a collar, and the radar sensor element 301 can be used to detect the pet's heartbeat value and respiration value. The inertial measurement unit 303 can be used to detect the tickling times and steps of the pet, and the global positioning system sensing element 304 can be used as a pet's location tracking, electronic fence or track recovery. In an embodiment, the comprehensive care device 1 can also be disposed on a pet sheet; wherein the radar sensor element 301 detects the state of the pet leaving the pet sheet, and the temperature sensor element 302 detects the pet's body temperature. In another embodiment, when the care object is an elderly, the comprehensive care device 1 can be combined with a mattress; wherein the radar sensing element 301 can detect the heartbeat value, breathing value and the state of leaving the mattress, and the pressure sensing element 305 detects the real-time turning state of the elderly.

Figure 4:
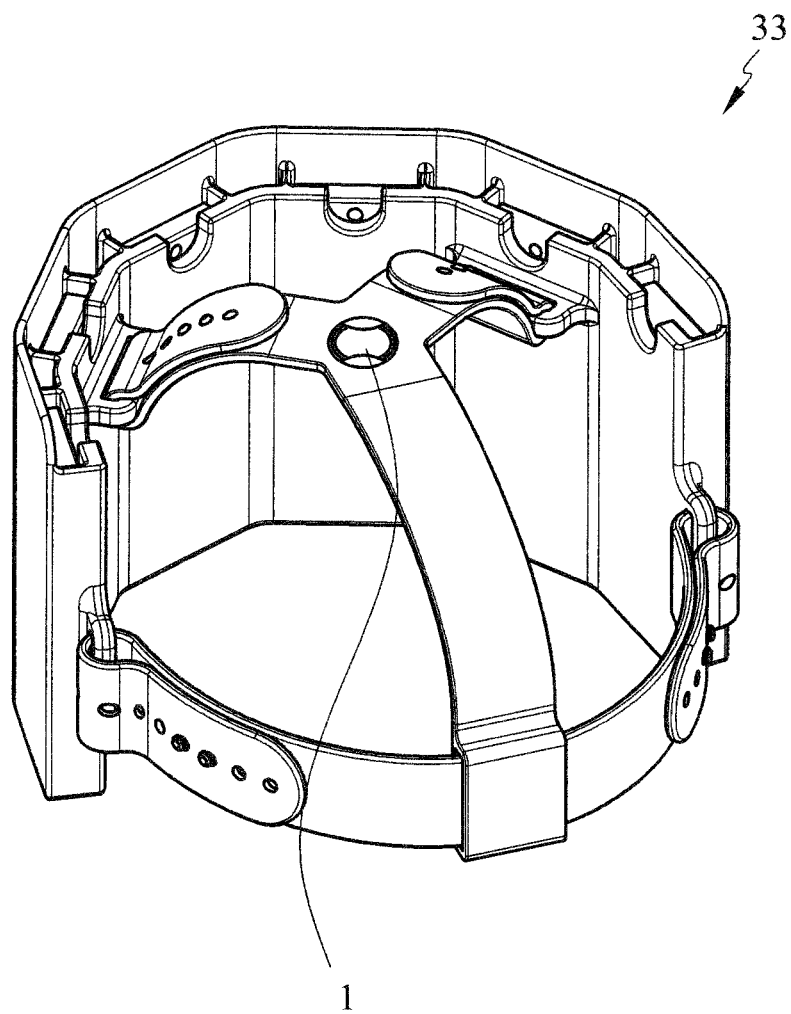
FIG. 4 is a structural diagram of a combination of the comprehensive care device and a head unit according to the first embodiment of the present invention.

Please refer to FIG. 4, FIG. 4 is a structural diagram of a combination of the comprehensive care device and a head unit according to the first embodiment of the present invention.

As shown in FIG. 2 and FIG. 4, the comprehensive care device 1 can also be combined with a head unit 33, which is a cervical spine rehabilitation adjustment device. The cervical spine rehabilitation adjustment device is capable of adjusting the number and weight of weight blocks to correct cervical vertebra, and a pressure detection value 3051 is detected through the pressure sensing element 305; wherein the pressure detection value 3051 shows the position of the weight blocks, the time of use and the usage frequency analysis. Secondly, the radar sensing element 301 is used to detect the heartbeat value and respiration value of a person wearing the head unit; and the head swing angle of the person wearing the head unit is detected through the inertial measurement unit 303.

Figure 5:
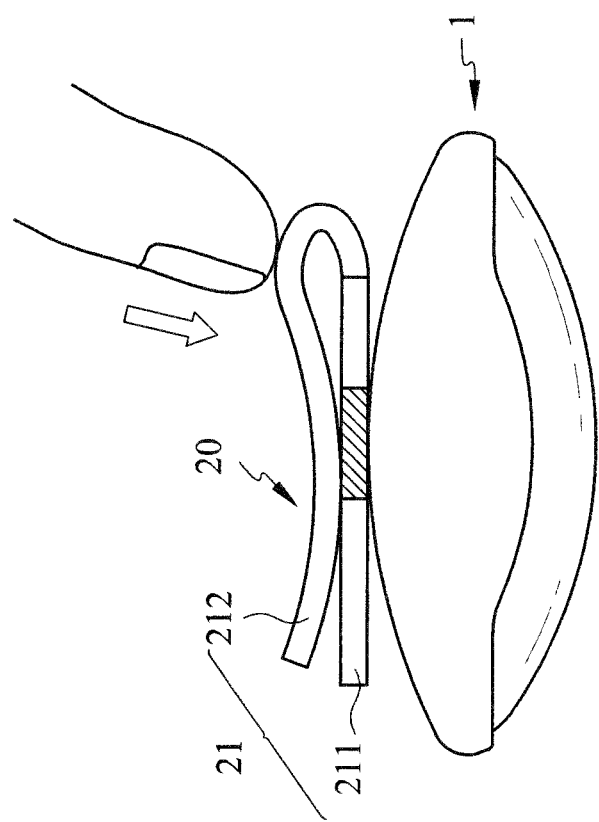
FIG. 5 is a structural diagram of the comprehensive care device according to the first embodiment of the present invention.

Please refer to FIG. 5, FIG. 5 is a structural diagram of the comprehensive care device according to the first embodiment of the present invention. As shown in FIG. 5, the fixing element 20 is an R-shaped clamp 21 composed of a first clamping piece 211 and a second clamping piece 212, and one end of the first clamping piece 211 is connected to one end of the second clamping piece 212. Further, the first clamping piece 211 of the R-shaped clamp 21 is fixed to the comprehensive care device 1, and the second clamping piece 212 can be pressed by a user to separate the first clamping piece 211 and the second clamping piece 212, so that the comprehensive care device 1 can be fixed on the clothing of the care object to prevent the comprehensive care device 1 from slipping down when the care object turns over.

Figure 6:
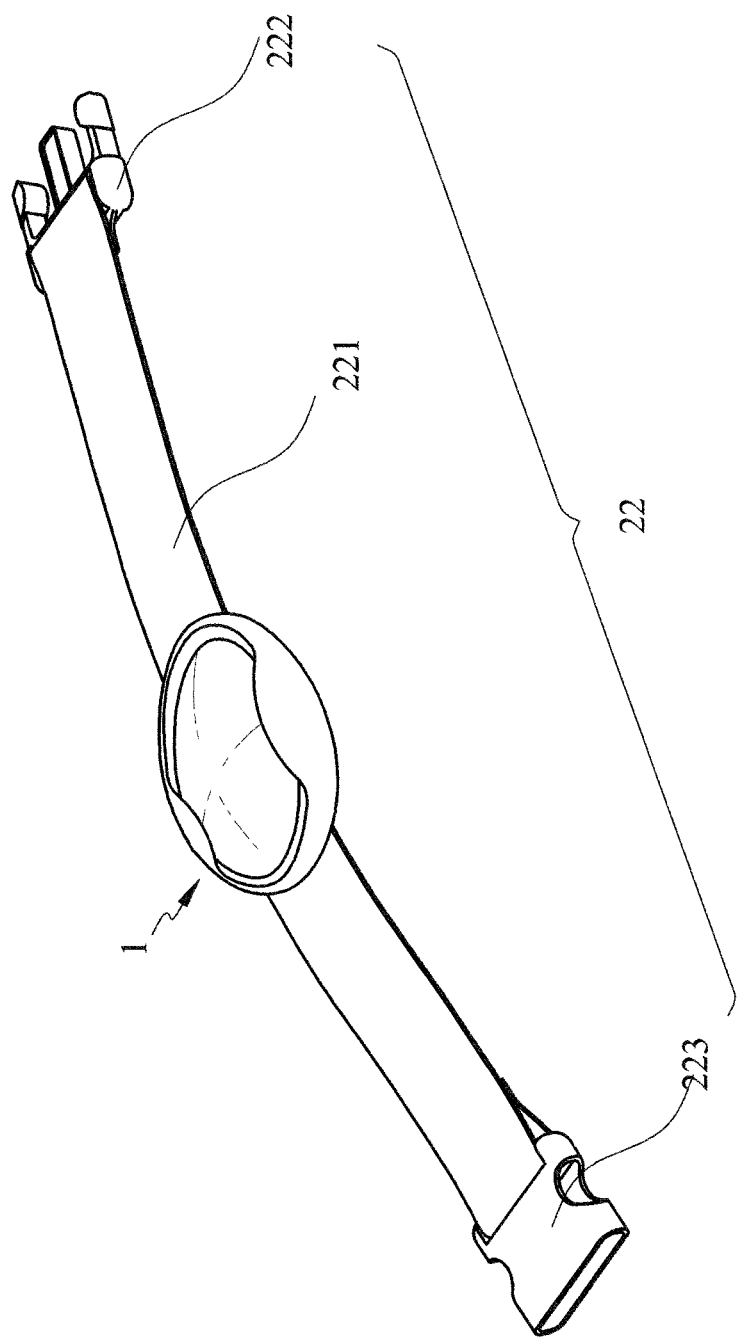
FIG. 6 is a structural diagram of the comprehensive care device according to the second embodiment of the present invention.

Please refer to FIG. 6, FIG. 6 is a structural diagram of the comprehensive care device according to the second embodiment of the present invention. As shown in FIG. 6, the fixing element 20 is the fixing structure 22 composed of a fixed belt 221, a male fastener 222 and a female fastener 223, the case 10 is fixed on the fixed belt 221, and the male fastener 222 is correspondingly fastened to the female fastener 223.

Figure 7:
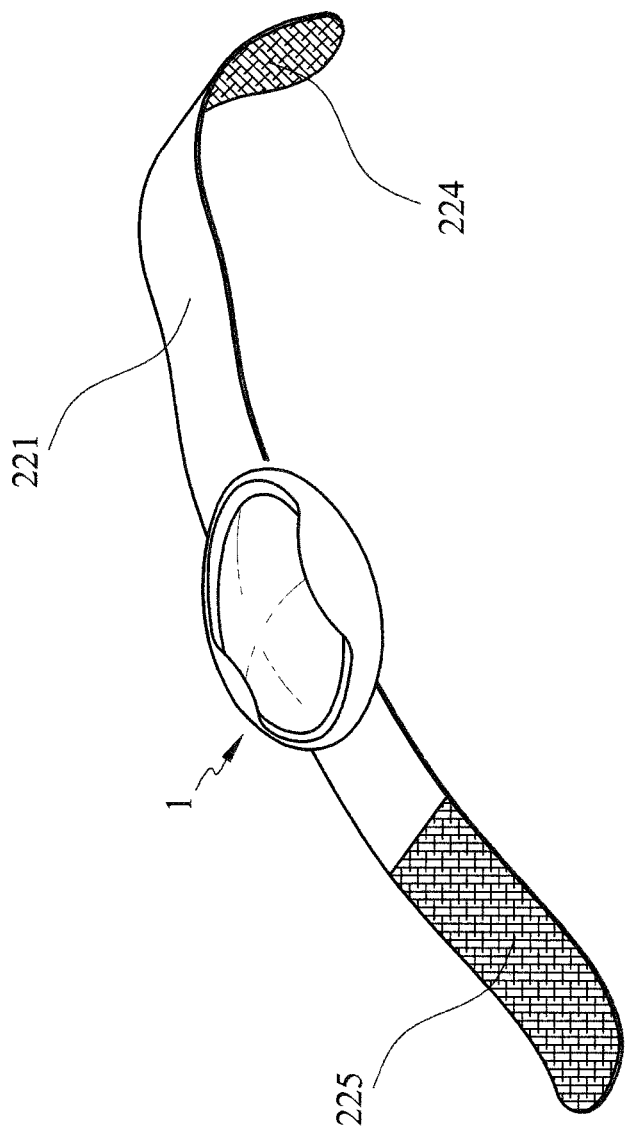
FIG. 7 is a structural diagram of the comprehensive care device according to a third embodiment of the present invention.

Please refer to FIG. 7, FIG. 7 is a structural diagram of the comprehensive care device according to a third embodiment of the present invention. As shown in FIG. 7, the Embodiment 3 is substantially the same in structure as the comprehensive care device described in the foregoing Embodiment 2, except that the fixing structure 22 is composed of a sticky part 224 and a bonding part 225 corresponding to the sticky part 224, and the sticky part 224 is correspondingly bonded to the bonding part 225 in the Embodiment 3.

The foregoing description, for the purpose of explanation, has been described with reference to specific embodiments; however. The embodiments were chosen and described in order to best explain the principles of the disclosure and its practical applications, to thereby enable others skilled in the art to best utilize the disclosure and various embodiments with various modifications as are suited to the particular use contemplated. The embodiments depicted above and the appended drawings are exemplary and are not intended to be exhaustive or to limit the scope of the disclosure to the precise forms disclosed. Modifications and variations are possible in view of the above demonstrations.

I claim:

1. A comprehensive care device, comprising:
a case having an accommodating space;
a fixing element disposed on an external surface of the case to be fixed on the clothing or body of a care object;
a plurality of sensing elements installed in the accommodating space, and each sensing element used to sense physiological state values of the care object to generate physiological state signals based on the physiological state values;

a storage element installed in the accommodating space and electrically connected to the sensing elements for storing the physiological state signals of the care object sensed by the sensing elements;

a processing element installed in the accommodating space and electrically connected to the storage element for receiving the physiological state signals of the care object stored in the storage element to perform a signal calculation, and then compare with a preset value to determine whether generate a warning signal or not;

a power supply element installed in the accommodating space and electrically connected to the sensing elements, the storage element and the processing element, so as to provide an electric power for an operation function of the comprehensive care device; and a data transmission element installed in the accommodating space and is electrically connected to the processing element and the power supply element, and the physiological state signals of the care object transmitted to a portable device through a wireless communication method; wherein when the processing element determines that the warning signal needs to be sent out, the data transmission element transmits the warning signal to the portable device, so that the portable device displays the warning signal, wherein the plurality of sensing element comprise at least a radar sensing element, wherein the radar sensing element measures a plurality of heartbeat values and a plurality of respiratory frequency at different times; the processing element receives the heartbeat values and the respiratory frequency and calculates them through the signal calculation to identify whether the heartbeat values and the respiratory frequency belong to a waking state or a sleeping state for a period of time; and the processing element analyzes the average and sum of sleep by detecting the time of the heartbeat values in the sleeping state.

2. The comprehensive care device in claim 1, wherein the portable device has a user interface for inputting an observation value of the care object by a user, and the observation value is transmitted to the processing element through the data transmission element; and the observation value and the physiological state signal are performed the signal calculation to compare with the preset value to determine whether the warning signal is generated or not.

3. The comprehensive care device in claim 1, wherein the sensing elements include at least one of a temperature sensing element, an inertial measurement unit, a global positioning system sensing element, and a pressure sensing element.

4. The comprehensive care device in claim 3, wherein the radar sensing element is used to sense a respiration value of the care object, and a respiratory frequency of the care object is calculated by the processing element to determine a respiration state of the care object; and when the processing element determines that the respiratory frequency is abnormal, the processing element generates the warning signal.

5. The comprehensive care device in claim 3, wherein the radar sensing element is used to sense a heartbeat value of the care object, and when the processing element determines that the heartbeat value exceeds a preset value, the processing element generates the warning signal.

6. The comprehensive care device in claim 3, wherein the inertial measurement unit is composed of three-axis gyroscopes and three-directional accelerometers, and is used to detect a tilt angle.

7. The comprehensive care device in claim 1, wherein the fixing element is a clamp or a fixing structure; the fixing structure comprises a fixed belt and a fastener, and the cast is fixed on the fixed belt, the fastener is composed of a male fastener and a female fastener, and the male fastener is correspondingly fastened to the female fastener.

8. The comprehensive care device in claim 7, wherein the fastener is composed of a sticky part and a bonding part corresponding to the sticky part, and the sticky part is correspondingly bonded to the bonding part.

9. The comprehensive care device in claim 1, wherein the wireless communication method is one of Bluetooth communication protocol, wireless network communication protocol, wireless RF communication, broadband network communication, Zigbee, Thread, 3G communication protocol or 4G communication protocol.

* * * * *